United States Patent
Jang et al.

(10) Patent No.: US 11,046,811 B2
(45) Date of Patent: Jun. 29, 2021

(54) COMPOUND FOR COPOLYMERIC POLYESTER RESIN, AND PREPARATION METHOD OF COPOLYMERIC POLYESTER RESIN USING THE SAME

(71) Applicant: Huvis Corporation, Seoul (KR)

(72) Inventors: Boo-Kyeong Jang, Daejeon (KR);
Hyun-Wook Shin, Gyeonggi-do (KR);
Seong-Yoon Park, Daejeon (KR);
Yo-Seung Ho, Daejeon (KR)

(73) Assignee: Hurvis Corporation, Seoul (KR)

( * ) Notice: Subject to any disclaimer, the term of this patent is extended or adjusted under 35 U.S.C. 154(b) by 0 days.

(21) Appl. No.: 15/569,183

(22) PCT Filed: Mar. 4, 2016

(86) PCT No.: PCT/KR2016/002181
§ 371 (c)(1),
(2) Date: Oct. 25, 2017

(87) PCT Pub. No.: WO2017/150750
PCT Pub. Date: Sep. 8, 2017

(65) Prior Publication Data
US 2019/0048133 A1  Feb. 14, 2019

(30) Foreign Application Priority Data

Mar. 2, 2016 (KR) .................. 10-2016-0025107

(51) Int. Cl.
*C08G 63/183* (2006.01)
*C08G 63/16* (2006.01)
*C07C 31/20* (2006.01)

(52) U.S. Cl.
CPC .......... *C08G 63/183* (2013.01); *C07C 31/20* (2013.01); *C08G 63/16* (2013.01)

(58) Field of Classification Search
CPC .. C08F 283/01; C08F 4/06; C08F 2220/1825; C08F 212/08; C08F 220/06; C08F 2220/1858; C08F 2220/281; C08F 299/0464; C08F 4/12; C08F 220/28; C08G 18/6696; C08G 18/68; C08G 18/6705; C08G 59/1438; C08G 59/5086; C08G 63/16; C08G 63/183; C07C 31/20
See application file for complete search history.

(56) References Cited

U.S. PATENT DOCUMENTS

| | | | | |
|---|---|---|---|---|
| 3,636,131 A * | 1/1972 | Davis | ............... | C08G 63/688 528/275 |
| 4,036,895 A | 7/1977 | Vogel et al. | | |
| 4,065,439 A | 12/1977 | Uno et al. | | |
| 4,129,675 A | 12/1978 | Scott | | |
| 4,415,727 A * | 11/1983 | Toga | ............... | C08G 63/183 264/523 |
| 5,912,307 A * | 6/1999 | Paschke | ............... | B65D 1/0207 525/444 |
| 5,916,677 A * | 6/1999 | Chen | ............... | C08G 63/183 264/176.1 |
| 6,103,857 A * | 8/2000 | Jones | ............... | C08G 63/199 528/271 |
| 6,362,306 B1 * | 3/2002 | Shelby | ............... | C08G 63/199 264/175 |
| 7,829,656 B2 | 11/2010 | Nichols et al. | | |

(Continued)

FOREIGN PATENT DOCUMENTS

| CN | 105131193 A | 9/2015 |
|---|---|---|
| JP | 2002-155260 A | 5/2002 |
| KR | 10-2006-0015651 A | 2/2006 |

(Continued)

OTHER PUBLICATIONS

"Modification of PET using MPDIOL Glycol", pp. 1-9; LyondellBasel tech Publication, 2011 attached.*
Rieckmann et al "Poly(Ethylene Terephthalate) Polymerization—Mechanism, Catalysis, Kinetics, Mass Transfer and Reactor Design" 2003 (Year: 2003).*
Bin Chen et al.,, "Thermal properties and chemical changes in blend melt spinning of cellulose acetate butyrate and a novel cationic dyeable copolyester", Journal of Applied Polymer Science, (Jan. 1, 2010), pp. NA-NA.

(Continued)

*Primary Examiner* — Ling Siu Choi
*Assistant Examiner* — Gennadiy Mesh
(74) *Attorney, Agent, or Firm* — Hammer & Associates, P.C.

(57) ABSTRACT

A method for preparing a thermal adhesive copolymerized polyester resin is disclosed. The method includes: a transesterification reaction in a reaction mixture of a diol compound according to Formula 1, for example, 2-Methyl-1,3-propanediol, an isophthalic acid (IPA) or an IPA derivative as an acid component, and polyethylene terephthalate; and a condensation polymerization reaction of the reaction mixture to prepare a copolymerized polyester resin. The copolymerized polyester resin has an intrinsic viscosity (I.V.) of 0.5 dL/g to 0.75 dL/g, a softening point (Ts) of 100° C. to 160° C., and a glass transition temperature (Tg) of 60° C. to 70° C. The copolymerized polyester resin can be effectively used in fields of clothing, automobile parts, as a thermal adhesive fiber.

[Formula 1]

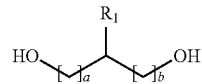

wherein $R_1$ is an alkyl group having 1 to 4 carbon atoms, a and b are each independently an integer ranging from 0 to 3, and each solid line represents a single bond when a and b is 0.

4 Claims, No Drawings

(56) References Cited

U.S. PATENT DOCUMENTS

2005/0163986 A1* 7/2005 Marlow ................ C08J 5/18
                                                                              428/220
2012/0226014 A1* 9/2012 Lee .................... B29C 55/08
                                                                              528/298

FOREIGN PATENT DOCUMENTS

| KR | 1020060015651 | 2/2006 |
| KR | 1020120126936 | 11/2012 |
| KR | 1020150025463 | 3/2015 |

OTHER PUBLICATIONS

Jaein Suh et al., "Melt spinning and drawing of 2-methyl-1,3-propanediol-substituted poly(ethylene terephthalate)," Journal of Applied Polymer Science, (vol. 88), No. 11, (Jun. 13, 2003), pp. 2598-2606.

Changfei Fu et al., "Structures and properties of easily dyeable copolyesters and their fibers respectively modified by three kinds of diols", Journal of Applied Polymer Science, (vol. 128, No. 6, (p. n/a-n/a), (Jan. 1, 2012).

* cited by examiner

COMPOUND FOR COPOLYMERIC POLYESTER RESIN, AND PREPARATION METHOD OF COPOLYMERIC POLYESTER RESIN USING THE SAME

TECHNICAL FIELD

The present invention relates to a compound for preparing a copolymerized polyester resin and a method for preparing a copolymerized polyester resin using the same.

BACKGROUND ART

In recent years, the role of a polyester fiber represented by polyethylene terephthalate (hereinafter referred to as "PET") in the field of textile fabrics such as non-woven fabrics and the like has been increasing. In this situation, the demand for thermal adhesive fibers that may be used in cloth adhesive cores, automotive interior materials, and the like has been increasing because a polyester resin capable of being thermally adhered at a temperature of 190° C. or lower and maintaining an adhesive property even at a temperature of less than 130° C. has been used as an adhesive component.

Therefore, research has been actively conducted to reduce a melting point of a polyester resin so that the polyester resin may be used as an adhesive component of a thermal adhesive fiber. For example, U.S. Pat. Nos. 4,129,675 and 4,065,439 disclose copolymerized polyester resins in which a diol compound such as ethylene glycol (EG), neopentyl glycol, and the like is copolymerized with a dicarboxylic acid such as terephthalic acid, isophthalic acid (IPA), adipic acid, sebacic acid, and the like.

However, copolymerized polyester resins that have so far been developed have drawbacks in that thermal fusion should be performed under a condition of a high temperature of 190° C. or higher, or the resins have poor workability as glass transition temperatures thereof decrease to less than 60° C. Also, IPA, which is used as the dicarboxylic acid to reduce melting points of the polyester resins, has problems in that an increase in manufacturing costs may be caused due to the high price of raw materials, and physical properties of a copolymerized polyester resin may be degraded because a cyclic compound (melting point: approximately 325±2° C.) having a degree of polymerization of 2 to 3 is formed as a byproduct thereof or workability may be degraded when thermal adhesive fibers are prepared therewith. Specifically, the cyclic compound is not melted in a polyester process because a melting temperature of the cyclic compound is greater than or equal to 300° C. Therefore, the cyclic compound, which functions as a foreign substance in a process, serves to extend a filtration cycle of polymers in a polymerization process and degrade processability in subsequent processes such as extrusion and injection and also serves as dust, thereby making a working environment difficult to work in.

DISCLOSURE

Technical Problem

Therefore, the present invention is designed to solve the problems of the prior art, and it is an object of the present invention to provide a method for preparing a copolymerized polyester resin having excellent workability and economic feasibility due to the fact that the copolymerized polyester resin may be thermally adhered at a temperature of 190° C. or lower, an adhesive property thereof is maintained even at a temperature of less than 130° C., and a content of a raw material such as isophthalic acid (IPA) therein is also controlled.

Technical Solution

To solve the above problems, according to an aspect of the present invention, there is provided a compound for preparing a copolymerized polyester resin which includes a compound represented by the following Formula 1:

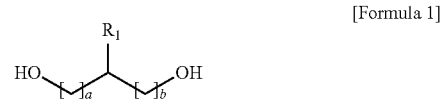

[Formula 1]

wherein $R_1$ is an alkyl group having 1 to 4 carbon atoms, a and b are each independently an integer ranging from 0 to 3, and each solid line represents a single bond when a and b is 0.

According to another aspect of the present invention, there is provided a method for preparing a copolymerized polyester resin, which includes polymerizing an acid component and a diol component to prepare a polyester resin, wherein the diol component includes a compound for preparing the resin, which is represented by the following Formula 1:

[Formula 1]

wherein $R_1$ is an alkyl group having 1 to 4 carbon atoms, a and b are each independently an integer ranging from 0 to 3, and each solid line represents a single bond when a and b is 0.

Advantageous Effects

The method for preparing a copolymerized polyester resin according to the present invention can be useful in exhibiting excellent processability and reducing manufacturing costs because the copolymerized polyester resin includes a compound represented by Formula 1 as a diol component. Also, the resin prepared according to the present invention can have excellent thermal adhesive strength even at a low temperature, and can also be advantageous in terms of workability and processability due to a decrease in byproducts produced in a polymerization process.

BEST MODE

The present invention may be embodied in many different forms and may have various embodiments, and thus particular embodiments thereof will be illustrated in the accompanying drawings and will be described in the detailed description.

However, it should be understood that the following detailed description is not intended to limit the present invention to specific embodiments of the present invention, but is rather intended to cover all modifications, similarities, and alternatives which are included in the spirit and scope of the present invention.

In the present invention, the terms "comprises," "comprising," "includes," "including," "has," and/or "having," when used herein, should be understood as specifying the presence of stated features, integers, steps, operations, elements, components, and/or combinations thereof, but not as precluding the presence or addition of one or more other features, integers, steps, operations, elements, components, and/or combinations thereof.

Also, in the present invention, the unit "part(s) by weight" refers to a weight ratio(s) between individual components.

In addition, in the present invention, the unit "molar part(s)" refers to a molar ratio(s) between individual components.

Further, in the present invention, the term "polymer" refers to an oligomer and/or a polymer obtained by polymerizing a monomer or a compound containing a polymerizable reactive group.

Hereinafter, the present invention will be descried in further detail.

According to one exemplary embodiment of the present invention, there is provided a compound for preparing a copolymerized polyester resin including a compound represented by the following Formula 1:

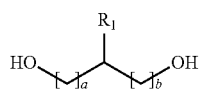

[Formula 1]

wherein $R_1$ is an alkyl group having 1 to 4 carbon atoms, and a and b are each independently an integer ranging from 0 to 3, and each of the solid lines represents a single bond when a and b is 0.

The compound for preparing a copolymerized polyester resin according to the present invention may include the compound represented by Formula 1, wherein the compound of Formula 1 has a structure in which an alkyl group represented by $R_1$, which functions as a side chain, is bound to an alkyl chain to which diol is bound as a diol component. Because the compound represented by Formula 1 contains the alkyl group represented by $R_1$ as the side chain, the compound may offer a space secured to rotate a main chain of a polymerized resin, thereby increasing a degree of freedom of the resin to reduce a melting point of the resin. This may have the same effect as using isophthalic acid (IPA) containing an asymmetric aromatic ring to reduce a melting point of a conventional crystalline polyester resin. Also, because the compound may be used to reduce a melting point of a polyester resin when the polyester resin is prepared instead of IPA, formation of a cyclic compound having a degree of polymerization of 2 to 3, which is derived from the IPA during polymerization of the polyester resin, may be prevented.

In this case, the compound for preparing a copolymerized polyester resin according to the present invention may include any compound without limitation as long as the compound is represented by Formula 1. Specifically, the compound for preparing a copolymerized polyester resin according to the present invention may include a compound in which $R_1$ in Formula 1 is a methyl group and a and b are each independently 1 or 2.

According to one exemplary embodiment, the compound represented by Formula 1 may be a compound represented by the following Formula 2.

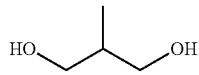

[Formula 2]

According to another exemplary embodiment of the present invention, there is provided a method for preparing a copolymerized polyester resin using a compound for preparing the copolymerized polyester resin according to the present invention.

The method for preparing a copolymerized polyester resin according to the present invention may include polymerizing an acid component and a diol component to prepare a polyester. In this case, the diol component may include the compound represented by Formula 1, and the polymerization may be performed using methods generally used in the related art.

The acid component may include terephthalic acid or a terephthalic acid derivative, and may optionally further include IPA or an IPA derivative. When the IPA or IPA derivative is further included, a content of the IPA or IPA derivative may be in a range of 1 to 40 molar parts, based on 100 molar parts of the acid component. Specifically, the content of the IPA or IPA derivative may be in a range of 1 to 30 molar parts, 5 to 25 molar parts, 5 to 20 molar parts, 5 to 15 molar parts, 15 to 25 molar parts, 25 to 35 molar parts, or 10 to 30 molar parts, based on 100 molar parts of the acid component.

Also, the diol component may include the compound represented by Formula 1 and one or more selected from the group consisting of ethylene glycol (EG) and diethylene glycol (DEG). Specifically, the diol component may include EG and the compound represented by Formula 1, and may optionally include both EG and DEG.

Here, a content of the compound represented by Formula 1 may be in a range of 1 molar part to 50 molar parts, based on 100 molar parts of the diol component. More specifically, the content of the compound represented by Formula 1 may be in a range of 5 molar parts to 40 molar parts, 10 molar parts to 30 molar parts, 20 molar parts to 40 molar parts, 25 molar parts to 50 molar parts, or 30 molar parts to 50 molar parts, based on 100 molar parts of the diol component. According to the present invention, when the content of the compound represented by Formula 1 is adjusted within this content range, a melting point of the resin may not be significantly degraded due to a low content of the compound, or degradation of physical properties of the resin may be prevented due to an excessive amount of the compound.

In addition, a content of the DEG may be in a range of 1 molar part to 20 molar parts, based on 100 molar parts of the diol component. Specifically, the content of the DEG may be in a range of 5 to 20 molar parts, 10 to 20 molar parts, 13 to 17 molar parts, 1 to 10 molar parts, 5 to 15 molar parts, or 4 to 16 molar parts, based on 100 molar parts of the diol component.

According to the present invention, when the content of the IPA additionally included as the acid component and the DEG additionally included as the diol component are adjusted within these content ranges, an increase in manufacturing costs of the copolymerized polyester resin may be prevented, and a glass transition temperature ($T_g$) of the copolymerized polyester resin may be reduced, thereby preventing the copolymerized polyester resin from changing over time in subsequent processes, for example, while spinning a copolymerized polyester, and the like.

Meanwhile, the copolymerized polyester resin prepared by the method according to the present invention may have a softening point $T_s$ of 100° C. to 160° C. Specifically, the copolymerized polyester resin may have a softening point $T_s$ of 110° C. to 160° C., 120° C. to 150° C., 120° C. to 140° C., 140° C. to 160° C., 100° C. to 130° C., 130° C. to 150° C., 120° C. to 125° C., 125° C. to 150° C., 125° C. to 140° C., 125° C. to 130° C., 127° C. to 146° C., 122° C. to 128° C., or 120° C. to 130° C.

Also, the copolymerized polyester resin may have a glass transition temperature $T_g$ of 50° C. or higher. Specifically, the glass transition temperature may be in a range of 50° C. to 80° C., and more specifically in a range of 50° C. to 60° C., 60° C. to 70° C., 70° C. to 80° C., 50° C. to 55° C., 55° C. to 60° C., 60° C. to 65° C., 65° C. to 70° C., 54° C. to 58° C., 58° C. to 68° C., 59° C. to 63° C., 55° C. to 70° C., 60° C. to 80° C., 65° C. to 80° C., or 67° C. to 79° C.

In addition, the copolymerized polyester resin may have an intrinsic viscosity I.V s of 0.5 dL/g to 0.75 dL/g. Specifically, the intrinsic viscosity I.V. may be in a range of 0.5 dL/g to 0.70 dL/g, 0.55 dL/g to 0.65 dL/g, 0.6 dL/g to 0.65 dL/g, 0.65 dL/g to 0.70 dL/g, 0.64 dL/g to 0.69 dL/g, 0.65 dL/g to 0.68 dL/g, 0.67 dL/g to 0.75 dL/g, 0.69 dL/g to 0.72 dL/g, 0.7 dL/g to 0.75 dL/g, or 0.63 dL/g to 0.67 dL/g.

Further, in the method for preparing a copolymerized polyester resin according to the present invention, the content of the IPA may be reduced by using the compound for preparing the resin, and a content of a cyclic compound having a degree of polymerization of 2 to 3, which is derived from the IPA during polymerization, may be accordingly reduced.

According to one exemplary embodiment, the resin may be included at a content of 1% by weight or less, based on the total weight of the cyclic compound having a degree of polymerization of 2 to 3. Specifically, the resin may be included at a content of 0.9% by weight or less, 0.8% by weight or less, 0.7% by weight or less, 0.6% by weight or less, 0.5% by weight or less, or 0.4% by weight or less.

MODE FOR INVENTION

Hereinafter, the present invention will be described in detail with reference to examples and experimental examples thereof.

However, it should be understood that the following examples and experimental examples proposed herein are given for the purpose of illustration only and are not intended to limit the scope of the present invention.

EXAMPLES 1 to 7

Terephthalic acid and ethylene glycol (EG) were added to an esterification bath, and the resulting mixture was subjected to a conventional polymerization reaction at 258° C. to prepare a polyethylene terephtalate polymer (i.e., a PET oligomer) having a reaction rate of approximately 96%. 2-Methyl-1,3-propanediol (MPD) represented by Formula 2, diethylene glycol (DEG), and isophthalic acid (IPA) were mixed with the prepared PET polymer at content ratios listed in the following Table 1. Thereafter, a transesterification catalyst was added thereto, and a transesterification reaction was then performed at 250±2° C. Then, a condensation polymerization catalyst was added to the resulting reaction mixture. While adjusting a final temperature and pressure in the esterification bath until the final temperature and pressure reached 280±2° C. and 0.1 mmHg, respectively, a condensation polymerization reaction was performed to prepare a copolymerized polyester resin.

TABLE 1

|  | MPD (molar parts) | DEG (molar parts) | IPA (molar parts) |
| --- | --- | --- | --- |
| Example 1 | 10 | — | — |
| Example 2 | 20 | — | — |
| Example 3 | 30 | — | — |
| Example 4 | 40 | — | — |
| Example 5 | 30 | 15 | — |
| Example 6 | 30 | — | 10 |
| Example 7 | 20 | — | 20 |

In Table 1, the contents (molar parts) of the individual components are calculated on the basis of a molar value (100 molar parts) of the PET oligomer.

COMPARATIVE EXAMPLE 1

The PET prepared in Example 1 was prepared as the control.

COMPARATIVE EXAMPLES 2 to 6

Copolymerized polyester resins were prepared in the same manner as in Example 1 except that IPA was mixed with the PET oligomer at content ratios as listed in the following Table 2 instead of the content ratios of Example 1 as listed in Table 1.

TABLE 2

|  | IPA (molar parts) | DEG (molar parts) |
| --- | --- | --- |
| Comparative Example 2 | 10 | — |
| Comparative Example 3 | 20 | — |
| Comparative Example 4 | 30 | — |
| Comparative Example 5 | 40 | — |
| Comparative Example 6 | 30 | 15 |

In Table 2, the contents (molar parts) of the individual components are calculated on the basis of the molar value (100 molar parts) of the PET oligomer.

EXPERIMENTAL EXAMPLE 1

To check physical properties of the resins prepared according to the present invention, glass transition temperatures $T_g$ of the resins prepared in Examples 1 to 7 and Comparative Examples 1 to 6 were measured using a differential scanning calorimeter (DSC-7, Perkin Elmer). Also, softening points $T_s$ of the resins were measured in a TMA mode using a dynamic mechanical analyzer (DMA-7, Perkin Elmer).

Also, each of the resins was dissolved at a concentration of 0.5% by weight in a solution in which phenol and tetrachloroethane were mixed at a weight ratio of 1:1, and intrinsic viscosities (I.V.) of the resins were measured at 35° C. using an Ubbelohde viscometer.

In addition, each of the resins were dissolved in trifluoroacetic acid (TFA), and filtered through a PTFE syringe filter (Diameter: 0.45 μm). Thereafter, $^1$H-NMR spectra of the resulting filtrates were measured using a nuclear magnetic resonance spectrometer (NMR, Bruker). The content of a cyclic compound having a degree of polymerization of 2 to 3 which remained in the resins was calculated from the results of the measurement. The results are listed in the following Tables 3 and 4.

TABLE 3

|  | MPD (molar parts) | DEG (molar parts) | IPA (molar parts) | $T_s$ (° C.) | $T_g$ (° C.) | I.V (dL/g) |
| --- | --- | --- | --- | --- | --- | --- |
| Example 1 | 10 | — | — | — | 78.4 | 0.68 |
| Example 2 | 20 | — | — | — | 74.8 | 0.67 |
| Example 3 | 30 | — | — | 145 | 71.2 | 0.65 |
| Example 4 | 40 | — | — | 128 | 67.6 | 0.6 |
| Example 5 | 30 | 15 | — | 121 | 61.8 | 0.72 |
| Example 6 | 30 | — | 10 | 126 | 67.2 | 0.68 |
| Example 7 | 20 | — | 20 | 124 | 66.8 | 0.69 |
| Comparative Example 1 | — | — | — | — | 82.1 | 0.66 |
| Comparative Example 2 | — | — | 10 | — | 78.0 | 0.69 |
| Comparative Example 3 | — | — | 20 | — | 74.6 | 0.65 |
| Comparative Example 4 | — | — | 30 | 142 | 72.6 | 0.68 |
| Comparative Example 5 | — | — | 40 | 120 | 69.8 | 0.66 |
| Comparative Example 6 | — | 15 | 30 | 115 | 63.5 | 0.61 |

TABLE 4

| | Content of Cyclic Compound (% by weight) | | Content of Cyclic Compound (% by weight) |
| --- | --- | --- | --- |
| Example 1 | ≤0.0001 | Comparative Example 2 | 0.25 |
| Example 2 | ≤0.0001 | Comparative Example 3 | 0.41 |
| Example 3 | ≤0.0001 | Comparative Example 4 | 0.56 |
| Example 4 | ≤0.0001 | Comparative Example 5 | 0.75 |
| Example 5 | ≤0.0001 | Comparative Example 6 | 0.63 |
| Example 6 | 0.17 | | |
| Example 7 | 0.36 | | |

As listed in Tables 3 and 4, it can be seen that, when the compound of the present invention represented by Formula 1 was included as the diol component of the polyester resin, thermal characteristics, such as the softening point $T_s$, the glass transition temperature $T_g$, and the like, of the prepared copolymerized polyester resin reached desired physical properties of resins capable of being thermally adhered at a low temperature. Also, it can be seen that workability and/or processability were improved due to a decrease in the content of the cyclic compound produced during resin preparation.

Specifically, looking at Table 3, it was found that the glass transition temperatures $T_g$ of the resins of Examples in which the compound represented by Formula 1 was included as the diol component decreased from 14.4° C. to approximately 3.7° C. as the content of the compound represented by Formula 1 increased from 10 molar parts to 40 molar parts, compared to that of the resin of Comparative Example 1 in which only terephthalic acid and EG were included as the acid component and the diol component. A similar pattern was observed for the softening points. From these results, it can be seen that the resins of Examples had effects equal to the resins of Comparative Examples in which the IPA or IPA derivative was included to improve thermal characteristics of conventional polyester resins.

Also, looking at Table 4, it was found that, because the resins of Examples 1 to 5 did not include IPA or a derivative thereof as the acid component, each of the resins included the cyclic compound having a degree of polymerization of 2 to 3, which was derived from the IPA or derivative thereof during polymerization, at a content of approximately 0.0001% by weight or less, which is approximately 2,500 times to 7,500 times lower than the resins of Comparative Examples 2 to 6 in which IPA, which is typically used to improve the thermal characteristics of the polyester resins, was included at the same content as that of the compound represented by Formula 1 in the resins of Examples 1 to 5.

From these results, it can be seen that the thermal characteristics of the resins were improved because the compound of the present invention represented by Formula 1 was included as the diol component during preparation of the copolymerized polyester resin. Therefore, because the IPA or derivative thereof was replaced with the compound of Formula 1, it was possible to reduce manufacturing costs and lower a content of the cyclic compound produced in a manufacturing process.

INDUSTRIAL APPLICABILITY

The method for preparing a copolymerized polyester resin according to the present invention can be useful in exhibiting excellent processability and reducing manufacturing costs because the copolymerized polyester resin includes the compound represented by Formula 1 as the diol component, and the resin thus prepared according to the present invention can have excellent thermal adhesive strength even at a low temperature, and can also be advantageous in terms of workability and processability due to a decrease in byproducts produced in a polymerization process. Therefore, the copolymerized polyester resin can be effectively used in fields of clothing, automobile parts, and the like in which the polyester resin is used as a thermal adhesive fiber.

The invention claimed is:
1. A method for preparing a thermal adhesive copolymerized polyester resin being capable of being thermal adhered at a temperature of 190° C. or lower, comprising the steps of:
performing a transesterification reaction at 250±2° C. in a reaction mixture in which a compound represented by the following formula 1 is added to polyethylene terephthalate; and
preparing a copolymerized polyester resin by performing a condensation polymerization reaction of the reaction mixture in which a transesterification is performed, at 280±2° C. and 0.1 mmHg,
wherein the reaction mixture in the step of performing a transesterification reaction, the reaction mixture further comprises a range of 5 to 25 molar parts of isophthalic acid (IPA) or an IPA derivative as an acid component, based on 100 molar parts of the acid component in polyethylene terephthalate,
wherein a content of the compound represented by Formula 1 is in a range of 20 molar part to 40 molar parts, based on 100 molar parts of the diol component in polyethylene terephthalate,
wherein the copolymerized polyester resin has an intrinsic viscosity (I.V.) of 0.5 dL/g to 0.75 dL/g,
wherein the copolymerized polyester resin has a softening point (Ts) of 100° C. to 160° C.,
wherein the copolymerized polyester resin has a glass transition temperature (Tg) of 60° C. to 70° C.,
wherein the copolymerized polyester resin includes at a content of 0.4% by weight or less of a cyclic compound having a degree of polymerization of 2 to 3, wherein the cyclic compound has a degree of polymerization of 2 to 3 is derived from isophthalic acid(IPA) or an IPA derivative in polymerization, wherein the cyclic compound has a degree of polymerization of 2 to 3 has melting point of 325±2° C.:

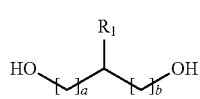

[Formula 1]

wherein $R_1$ is an alkyl group having 1 to 4 carbon atoms,
a and b are each independently an integer ranging from 0 to 3, and
each solid line represents a single bond when a and b is 0.

2. The method of claim 1, wherein $R_1$ is a methyl group, and a and b are each independently 1 or 2.

3. The method of claim 1, wherein the compound represented by Formula 1 is a compound represented by the following Formula 2

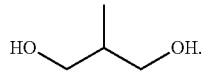

[Formula 2]

4. The method of claim 1, wherein the reaction mixture further comprises a range of 10 to 20 molar parts of diethylene glycol as a diol component, based on 100 molar parts of the diol component in polyethylene terephthalate.

* * * * *